United States Patent [19]

Davidson

[11] Patent Number: 4,670,579

[45] Date of Patent: Jun. 2, 1987

[54] TELOMERIZATION OF OLEFINS

[75] Inventor: Robert I. Davidson, Baton Rouge, La.

[73] Assignee: Ethyl Corporation, Richmond, Va.

[21] Appl. No.: 880,071

[22] Filed: Jun. 30, 1986

[51] Int. Cl.$^4$ .................. C07C 67/347; C07C 107/06; C07C 17/22

[52] U.S. Cl. ...................................... 560/83; 534/587; 534/885; 560/81; 560/96; 560/105; 560/202; 570/206

[58] Field of Search .................. 560/202, 83, 81, 105, 560/96; 534/587, 885; 570/206

[56] References Cited

PUBLICATIONS

Doyle et al, *J. Org. Chem.*, vol. 42, No. 14, pp. 2431–2436, (1977).

Kawamatsu et al, *Arzneim.-Forsch./Drug Res.*, vol. 30(I), No. 5, pp. 751–758, (1980).

Freidlina et al, Doklady Akadomii Nauk 555R, vol. 183, No. 5, pp. 1113–1116, (1968), (translation).

Rondestvedt I, *Organic Reactions*, vol. 11, pp. 189–260.

Rondestvedt II, *Organic Reactions*, vol. 24, pp. 225–259.

*Primary Examiner*—Natalie Trousof
*Assistant Examiner*—Vera C. Clarke
*Attorney, Agent, or Firm*—Donald L. Johnson; John F. Sieberth; Patricia J. Hogan

[57] ABSTRACT

An olefin, especially an activated olefin, is telomerized by reaction with an arylamine, such as an aniline, in the presence of an alkyl nitrite, a copper catalyst, and a catalytic amount of water and/or acid and in the absence of more than about 0.5 volume part of inert solvent per volume part of olefin.

9 Claims, No Drawings

TELOMERIZATION OF OLEFINS

FIELD OF THE INVENTION

This invention relates to the telomerization of olefins and more particularly relates to a Meerwein-type reaction for effecting the telomerization.

BACKGROUND

It is known that olefins can be arylated by Meerwein-type reactions. In the conventional two-step Meerwein reaction, an arylamine is converted to a diazonium salt which is then reacted with the olefin in the presence of a copper catalyst. In the one-step Meerwein-type reaction, the olefin is treated directly with the arylamine and a nitrite rather than with a diazonium salt. The latter type of reaction is taught in Doyle et al., *J. Org. Chem.*, Vol. 42, 1977, pp. 2431-2436; Kawamatsu et al., *Arzneim.Forsch./Drug.*, Res., Vol 30(I), No. 5, 1980, pp. 751-58; and copending application Ser. No. 758,818 (Davidson), filed July 25, 1985.

As indicated in Freidlina et al., *Doklady Akademii Nauk SSSR*, Vol. 183, No. 5, 1968, pp. 1113-1116, it has been recognized that it would be desirable to be able to accomplish some telomerization in Meerwein reactions but that most Meerwein reactions do not permit telomers to be formed. It has been theorized that it is the presence of the copper catalyst which prevents chain growth in Meerwein reactions. However, regardless of the nature of the chain growth inhibitor, Freidlina et al. found that its inhibitory effect could be overcome in a conventional Meerwein reaction by the use of sodium acetate and an excess of the olefin. Kawamatsu et al. show that a small amount of telomerization occurs in their one-step Meerwein-type reaction, but they do not teach what permitted the telomerization to occur.

SUMMARY OF INVENTION

An object of this invention is to provide a novel process for telomerizing olefins.

Another object is to provide such a process wherein the telomerized olefins are prepared by a one-step Meerwein reaction.

These and other objects are attained by reacting an arylamine with an excess of an olefin in the absence of more than about 0.5 volume part of inert solvent per volume part of olefin and in the presence of an alkyl nitrite, a copper catalyst, and a catalytic amount of water and/or acid.

DETAILED DESCRIPTION

Arylamines that can be used in the process of the invention may be generally described as the arylamines already known to be capable of being used in Meerwein-type arylation reactions. Such arylamines are compounds having an amino group attached to an aromatic (e.g., phenyl, naphthyl, pyridyl, thiazolyl, etc.) ring which optionally bears one or more other substitutents, such as a chloro, fluoro, cyano, nitro, amino, substituted amino, or an optionally-substituted —R, —OR, —SR, or —COOR substitutent wherein R is alkyl, cycloalkyl, or aryl. Any organic substituents on the ring generally contain up to about 40 carbons, most commonly 1-6 carbons.

Exemplary of the arylamines that can be used are aniline, 4-methoxyaniline, 3,4-dimethoxyaniline, 3,4,5-trimethoxyaniline, 4-(2-methyl-2-phenylpropyloxy)aniline, 4-nitroaniline, 4-acetylaniline, 4-chloroaniline, 2,4-dichloroaniline, 4-methylaniline, p-phenylenediamine, benzidine, p-aminobiphenyl, 3-aminoquinoline, 5-nitro-2-aminothiazole, aminonaphthalene, etc., as well as the other arylamines taught in Doyle et al., Kawamatsu et al., and the references cited therein (especially Rondestvedt, *Organic Reactions*, Vol. 11, pp. 189-260, and Rondestvedt, *Organic Reactions*, Vol. 24, pp. 225-259), all of which are incorporated herein in toto by reference.

Olefins utilizable in the process are also generally describable as those already known to be capable of being used in Meerwein-type arylation reactions. Such olefins include simple alkenes, such as ethylene, but are preferably activated olefins, i.e., olefins wherein the ethylenic bond is activated by being attached to an electron-withdrawing group, such as carbonyl, cyano, halo, aryl, vinyl, etc. Exemplary of such olefins are quinones; unsaturated nitriles, such as acrylonitrile, methacrylonitrile, ethacrylonitrile, etc.; unsaturated acids and esters, such as acrylic acid, methacrylic acid, maleic acid, cinnamic acid, etc., and their methyl, higher alkyl, cycloalkyl, and aryl esters; conjugated dienes, such as butadiene, isoprene, etc.; aryl olefins, such as styrene, 4-methylstyrene, etc.; unsaturated halides, such as vinyl chloride, vinylidene chloride, etc.; unsaturated aldehydes, such as acrolein, methacrolein, etc.; as well as the other activated olefins taught by Doyle et al., Kawamatsu et al., and the Rondestvedt references.

The amount of olefin employed is an excess and is generally at least about 5, preferably at least about 13, mol equivalents per mol equivalent of amino groups in the arylamine. There is no maximum to the amount of olefin that may be used, and it is frequently desirable to use a considerable excess so that the olefin can also function as the sole solvent for the reaction mixture. However, as a practical matter, the amount utilized is usually in the range of about 5-40 mol equivalents.

The alkyl nitrite may be any alkyl nitrite capable of diazotizing the arylamine in situ but is generally an alkyl nitrite containing 1-6 carbons, such as the methyl, ethyl, n-propyl, isopropyl, n-butyl, isobutyl, t-butyl, isoamyl, and hexyl, etc., nitrites. The amount of alkyl nitrite used should be at least the substantially stoichiometric amount, i.e., an amount slightly in excess of the amount required to react with the arylamine, and is generally in the range of about 1.25-1.5 mol equivalents per mol equivalent of amino groups in the arylamine. More alkyl nitrite can be employed without deleteriously affecting the process, but a large excess of the nitrite is unnecessary and uneconomical.

As mentioned above, the reaction is conducted in the presence of a copper catalyst and a catalytic amount of water and/ or acid.

The copper catalyst may be any of the copper catalysts conventionally employed in Meerwein-type reactions, but the catalysts that are preferred are the more available catalysts, such as copper powder, cuprous or cupric oxide, cuprous or cupric chloride, cuprous or cupric bromide, etc., with cupric chloride dihydrate being particularly preferred as an available compound that provides both the copper and co-catalyst desired. The amount employed is generally about 0.05-2 mol equivalents, most commonly about 0.1-1.0 mol equivalent, based on the number of amino groups present, the amount that is particularly useful varying with the reactivities of the reactants being used.

The acid, when employed, may be an inorganic or organic acid, such as hydrochloric, sulfuric, phosphoric, acetic, chloroacetic, trichloroacetic, benzoic, methanesulfonic, etc.; and it is typically used in amounts such as those in which the copper catalyst is employed. The water, when employed, may be incorporated into the reaction mixture alone, as the solvent for the acid, or as part of the copper catalyst molecule and—like the acid—is generally used in amounts such as those in which the copper catalyst is employed. Most commonly, the acid and/or water used in the reaction is utilized in an amount from about 1–15 times the amount of copper catalyst employed, although larger amounts can be used if desired.

The solvents that may be employed in the reaction are inert polar organic solvents, such as acetonitrile, acetone, methyl ethyl ketone, N-methylpyrrolidone, pyridine, tetrahydrofuran, dimethyl sulfoxide, etc., i.e., solvents of the type conventionally used in Meerwein arylation reactions. However, as indicated above, minimization of the amount of solvent enhances telomerization, so the reaction is typically conducted in the absence of any solvent other than excess olefin or in the presence of up to only about 0.5 volume part of inert solvent per volume part of olefin. It is generally preferred that the amount of any inert solvent be not more than about 0.3 volume part per volume part of olefin.

The reaction is conducted by combining the aforementioned and any optional ingredients in any convenient manner and maintaining them in contact with one another, generally with stirring, for a suitable time, e.g., about 1–3 hours. Ordinarily, it is preferred to conduct the reaction at ambient temperature, e.g., about 20°–45° C., although cooling may be used if too much heat is generated by the reaction. After completion of the reaction, the telomer may be recovered by distillation when separation from by-products is desired.

The invention is advantageous as a means of providing telomerized olefins in improved yields by a one-step Meerwein reaction. The products are primarily useful as intermediates for materials such as flavorings, perfumes, cosmetics, polymers, pharmaceuticals, etc., which may be prepared from the products in essentially the same manner as from the corresponding untelomerized products.

The following examples are given to illustrate the invention and are not intended as a limitation thereof.

EXAMPLE I

A mixture of 0.026 mol of trichloroacetic acid, 50 mL (0.555 mol) of methyl acrylate, 0.015 mol of magnesium sulfate, 0.025 mol of aniline, and 0.0075 mol of cupric chloride dihydrate was stirred at 5° C. under nitrogen, and a solution of 0.033 mol of isopropyl nitrite in 10 mL (0.11 mol) of methyl acrylate was added over 30 minutes. The resulting mixture was stirred at ambient temperature for two hours and then worked up and concentrated to afford 11.7 g of a brown oil. VPC analysis of the oil showed that the reaction resulted in a 40.9% yield of methyl 2-chloro-3-phenylpropionate, a 21.9% yield of diesters (i.e., telomers having two methyl acrylate-derived segments in a chain terminated by a phenyl group), and an 8.4% yield of triesters (i.e., telomers having three methyl acrylate-derived segments in a chain terminated by a phenyl group). The major telomer was dimethyl 2-benzyl-4-chloroglutarate.

EXAMPLE II

A mixture of 0.037 mol of isopropyl nitrite, 50 mL (0.555 mol) of distilled methyl acrylate, 0.025 mol of cupric chloride dihydrate, and 13 mL (0.25 mol) of acetonitrile was stirred under nitrogen at ambient temperature. A solution of 0.025 mol of distilled aniline and 15 mL (0.167 mol) of distilled methyl acrylate was added dropwise over 20 minutes. The temperature rose to 40° C., and stirring was continued at ambient temperature for two hours. The reaction mixture was then worked up and concentrated to afford 16.52 g of product. VPC analysis showed that the reaction resulted in a yield of 63.3% of methyl 2-chloro-3-phenylpropionate, 13.7% of diesters, 2.3% of triesters, and 4.8% of chlorobenzene.

COMPARATIVE EXAMPLE

A mixture of 0.025 mol of distilled aniline, 30 mL of acetonitrile, 29.5 mL (0.327 mol) of distilled methyl acrylate, and 0.025 mol of cupric chloride dihydrate was stirred under nitrogen. A mixture of 0.0375 mol of isopropyl nitrite and 30 mL of acetonitrile was added over 25 minutes, and stirring was continued for two hours. The reaction mixture was then worked up and concentrated to afford 11.09 g of a brown solution. VPC analysis showed that the reaction resulted in a yield of 64.4% of methyl2-chloro-3-phenylpropionate, 14.6% of chlorobenzene, 4.1% of azobenzene, and only 0.8% of diester telomers.

It is obvious that many variations can be made in the products and processes set forth above without departing from the spirit and scope of this invention.

What is claimed is:

1. In a process for reacting an arylamine with an excess of an olefin in the presence of an alkyl nitrite and a copper catalyst, the improvement which comprises enhancing telomerization of the olefin by conducting the reaction in the presence of not more than about 0.0–0.5 volume part of inert solvent per volume part of olefin and in the presence of a catalytic amount of water and/or acid.

2. The process of claim 1 wherein the arylamine is an aniline.

3. The process of claim 2 wherein the aniline is aniline.

4. The process of claim 1 wherein the olefin is an olefin wherein the ethylenic bond is activated by an electron-withdrawing group.

5. The process of claim 4 wherein the activated olefin is methyl acrylate.

6. The process of claim 1 wherein the catalyst is cupric chloride dihydrate.

7. The process of claim 1 wherein the reaction is conducted in athe presence of not more than about 0.0–0.3 volume part of inert solvent per volume part of olefin.

8. The process of claim 1 wherein the reaction is conducted in the absence of any inert solvent.

9. The process of claim 1 wherein aniline is reacted with methyl acrylate in the presence of an alkyl nitrite and cupric chloride dihydrate.

* * * * *

UNITED STATES PATENT AND TRADEMARK OFFICE
CERTIFICATE OF CORRECTION

PATENT NO.   : 4,670,579
DATED        : JUNE 2, 1987
INVENTOR(S)  : ROBERT I. DAVIDSON

It is certified that error appears in the above-identified patent and that said Letters Patent is hereby corrected as shown below:

Face Page, Second Column, reads "Nauk 555R" and should read -- Nauk SSSR --.

Column 4, line 30, reads "methyl2" and should read -- methyl 2 --.

Column 4, line 50, reads "activated by an" and should read -- activated by being attached to an --.

Column 4, line 57, reads "in athe presence" and should read -- in the presence --.

Signed and Sealed this

Twentieth Day of October, 1987

Attest:

DONALD J. QUIGG

Attesting Officer

Commissioner of Patents and Trademarks